United States Patent
Lizio et al.

(10) Patent No.: US 8,951,558 B2
(45) Date of Patent: Feb. 10, 2015

(54) AQUEOUS CARBONATED MEDIUM CONTAINING AN AMINO(METH)ACRYLATE POLYMER OR COPOLYMER

(75) Inventors: Rosario Lizio, Dieburg (DE); Michael Damm, Roedermark (DE); Hans-Ulrich Petereit, Darmstadt (DE)

(73) Assignee: Evonik Röhm GmbH, Darmstadt (DE)

( * ) Notice: Subject to any disclaimer, the term of this patent is extended or adjusted under 35 U.S.C. 154(b) by 96 days.

(21) Appl. No.: 13/322,530

(22) PCT Filed: Jul. 30, 2009

(86) PCT No.: PCT/EP2009/059853
§ 371 (c)(1),
(2), (4) Date: Nov. 25, 2011

(87) PCT Pub. No.: WO2011/012162
PCT Pub. Date: Feb. 3, 2011

(65) Prior Publication Data
US 2012/0087977 A1   Apr. 12, 2012

(51) Int. Cl.
| | |
|---|---|
| A61K 9/48 | (2006.01) |
| A61K 9/32 | (2006.01) |
| A61K 9/16 | (2006.01) |
| A61K 9/50 | (2006.01) |
| A23G 3/02 | (2006.01) |
| A23L 1/30 | (2006.01) |
| A23L 3/015 | (2006.01) |
| A23P 1/00 | (2006.01) |
| B29D 22/00 | (2006.01) |
| B29D 23/00 | (2006.01) |
| B32B 1/08 | (2006.01) |
| B32B 27/08 | (2006.01) |
| A61K 47/32 | (2006.01) |
| C08F 8/30 | (2006.01) |
| C08L 39/00 | (2006.01) |
| A61K 47/08 | (2006.01) |

(52) U.S. Cl.
CPC ..................... A61K 47/08 (2013.01)
USPC ........... 424/463; 424/482; 424/497; 426/512; 426/648; 426/665; 428/34.1; 428/35.7; 514/772.6; 524/555

(58) Field of Classification Search
CPC ..................................................... A61K 47/08
USPC .......... 424/463, 482, 497, 684; 426/512, 665, 426/64; 428/34.1, 35.7; 514/772.6; 524/555
See application file for complete search history.

(56) References Cited

U.S. PATENT DOCUMENTS

| 5,686,062 A * | 11/1997 | Tong ............................... 424/47 |
| 6,214,319 B1 * | 4/2001 | Franzke et al. ................. 424/47 |
| 6,689,339 B1 | 2/2004 | Tanaka et al. |
| 8,399,523 B2 * | 3/2013 | Langguth et al. .......... 514/772.6 |
| 2007/0098801 A1 * | 5/2007 | Verreck et al. ................ 424/489 |
| 2008/0306233 A1 | 12/2008 | Muhrer et al. |
| 2009/0221761 A1 | 9/2009 | Muhrer et al. |

FOREIGN PATENT DOCUMENTS

| CN | 1278733 A | 1/2001 |
| CN | 101326200 A | 12/2008 |
| EP | 1 043 023 | 10/2000 |
| WO | 2005 023215 | 3/2005 |
| WO | 2007 071356 | 6/2007 |

OTHER PUBLICATIONS

Evonik (Eudragit® RS100 [Retrieved from internet <URL: http://eudragit.evonik.com/product/eudragit/en/products-services/eudragit-products/sustained-release-formulations/rs-100/Pages/default.aspx >] [Downloaded Oct. 22, 2013]), 2 pages.*
USP (USP/NF, United States Pharmacopeia/National Formulary, vol. 35, Chapter <661> Containers—Plastic [Downloaded Oct. 28, 2013] [Retrieved from internet <URL: https://mc.usp.org/sites/default/files/documents/GeneralChapterPDFs/661ContainersPlastic.pdf >]), 5 pages.*
International Preliminary Report on Patentability for PCT/EP2009/059853, the instant application. (Jan. 31, 2012), 5 pages.*
Cotter, Reactions [Retrieved from internet <URL: http://dl.clackamas.cc.or.us/ch106-05/reaction.htm >] [Downloaded Mar. 14, 2014]., (4 pages).*
Rafati et al., A New Solution for a Chronic Problem; Aqueous Enteric Coating, Journal of Pharmaceutical Sciences (Nov. 2006), 95 (11): 2432-2437, (6 pages).*
Document 200800043, the body of the international priority application as originally filed, per WIPO and as published on Feb. 3, 2011, 30 pages.*
Garay et al. (Polymeric microparticles prepared by supercritical antisolvent precipitation, Powder Technology (2010) (available online Sep. 28, 2009) 197: 211-217), 7 pages.*
Evonik, Eudragit E 100, Product Information, [Retrieved Oct. 22, 2013], 2 pages.*

(Continued)

Primary Examiner — Jason Sims
Assistant Examiner — Miriam A Levin
(74) Attorney, Agent, or Firm — Oblon, Spivak, McClelland, Maier & Neustadt, L.L.P.

(57) ABSTRACT

The invention relates to an aqueous medium containing an amino(meth)acrylate polymer or copolymer which is not soluble in dematerialised water, characterized in that the medium has a content of an aqueous phase of at least 60% by weight and a content of up to 40% by weight of solids comprising the amino(meth)acrylate polymer or copolymer, whereby the aqueous phase is charged by a sufficient amount of carbon dioxide that effects the amino(meth)acrylate polymer or copolymer to be present in solute form in the medium. The aqueous medium may be used beneficially as a coating or binding solution for the spray coating or binding of pharmaceutical compositions or nutraceutical compositions or cosmetical compositions.

14 Claims, No Drawings

(56) References Cited

OTHER PUBLICATIONS

Squillante III et al, Supercritical Fluid, Extended-Release Chlorpheniramine Maleate From Polymethacrylate Solid Dispersions by Supercritical Fluid Processing, Drug Delivery Technology (2002) 2(5): 58-64. (7 pages).*

Combined Chinese Office Action and Search Report issued Jan. 5, 2013 in Chinese Patent Application No. 200980159957.8 (with English-language translation).

Nikitine, C. et al., "Residence Time Distribution of a Pharmaceutical Grade Polymer Melt in a Single Screw Extrusion Process", Chemical Engineering Research and Design, vol. 87, No. 6, pp. 809-816, XPO2612917, (Jun. 1, 2009).

Stithit, S. et al., "Development and Characterization of Buoyant Theophylline Microspheres with Near Zero Order Release Kinetics", Journal of Microencapsulation, vol. 15, No. 6, pp. 725-737, XP000783454, (Nov. 1, 1998).

International Search Report issued Apr. 14, 2010 in PCT/EP2009/059853 filed Jul. 30, 2009.

* cited by examiner

AQUEOUS CARBONATED MEDIUM CONTAINING AN AMINO(METH)ACRYLATE POLYMER OR COPOLYMER

CROSS REFERENCE TO RELATED APPLICATION(S)

This application is a 35 U.S.C. §371 national stage patent application of international patent application PCT/EP09/059853, filed Jul. 30, 2009, the text of which is incorporated herein by reference.

FIELD OF THE INVENTION

The invention refers to the field of aqueous solutions or dispersions containing amino (meth)acrylate polymers or copolymers to be used in pharmaceutical, nutraceutical or cosmetic formulations.

TECHNICAL BACKGROUND

Amino(meth)acrylate polymer or copolymers are well known to be used for instance as coating or binding agents in the field of Pharmacy (U.S. Pat. No. 4,705,695). Amino (meth)acrylate polymer or copolymers can be for instance composed of polymerized units of 30 to 80% by weight of $C_1$- to $C_4$-alkyl esters of acrylic or of methacrylic acid and 70 to 20% by weight of alkyl(meth)acrylate monomers having a tertiary amino group in the alkyl radical. EUDRAGIT® E and EUDRAGIT® EPO are examples for these kind of polymer or copolymers and composed of polymerized units of 25% by weight of methyl methacrylate, 25% by weight of butyl methacrylate and 50% by weight of dimethylaminoethyl methacrylate.

These kind of polymers are soluble in organic solvents but insoluble in pure or demineralised water. Amino(meth)acrylate polymers or copolymers are soluble in aqueous buffered media below pH 5.0 but insoluble at higher pH values. Thus Amino(meth)acrylate polymer or copolymers are often used for the coating of pharmaceutical compositions to realize a taste masking effect in the mouth combined with a rapid active ingredient release in the stomach. Amino(meth)acrylate polymer or copolymers may also show positive effects on the storage stability of pharmaceutical compositions due to prevention of moisture uptake.

The coating with amino(meth)acrylate polymers or copolymers can be easily applied from organic solutions by spray applications. However organic solutions are nowadays more and more avoided due to general environmental and health considerations. Therefore aqueous dispersions of coating solutions are usually preferred over organic solutions.

In the case of amino(meth)acrylate polymers or copolymers stable aqueous dispersions can be produced by partially neutralization of the aminogroups in the polymer or copolymers by the addition of acids (U.S. Pat. No. 4,705,695). However the addition of pure acids like HCl for instance may deminish the taste masking ability or the positive effects on the storage stability. Sometimes the use in powder forms and the addition of certain emulgators or fatty organic acids or alcohols may help to overcome these problems.

WO02067906A1 (U.S.20030064036A1) for instance describes a coating and binding agent with improved storage stability, consisting essentially of (a) a polymer or copolymer, consisting of radically polymerized $C_1$- to $C_4$-alkyl esters of acrylic or methacrylic acid and other alkyl(meth)acrylate monomers which comprise functional tertiary amino groups, the polymer or copolymer being in the form of a powder with an average particle size of 1-40 μm, (b) 3-15 wt. %, based on (a), of an emulsifier with a HLB value of at least 14, (c) 5-50 wt. %, based on (a), of a $C_{12}$-$C_{18}$-monocarboxylic acid or a $C_{12}$-$C_{18}$-hydroxyl compound.

One of the beneficial effects of the invention is effective taste masking and that the vapour permeability is reduced. Dispersion processing times of the inventive examples are around 3 to 6 hours. However sometimes the use of the amino(meth)acrylate polymer or copolymers in powder form may cause problems with dust. There is also a general trend to avoid the addition at least of larger amounts of excipients.

PROBLEM AND SOLUTION

It was an object of the present invention to provide stable aqueous forms of amino (meth)acrylate polymers or copolymers that avoid the problems as discussed before.

The problem is solved by an aqueous medium containing an amino(meth)acrylate polymer or copolymer which is not soluble in demineralised water, characterized in that the medium has a content of the aqueous phase of at least 60% by weight and a content of solids of up to 40% by weight comprising the amino(meth)acrylate polymer or copolymer, whereby the aqueous phase is charged by a sufficient amount of carbon dioxide that effects the amino(meth)acrylate polymer or copolymer to be present in solute form in the medium.

It was surprisingly found that an aqueous medium carbonated with carbon dioxide can be used to realize a solution or a dispersion of an amino(meth)acrylate polymer or copolymer. It has been demonstrated that the amino groups are at least partially neutralized by the carbonic acid/hydrogen carbonate dissolved in the aqueous phase and thus the amino (meth)acrylate polymer or copolymer becomes at least dispersed, partially dissolved or even completely dissolved or something in between these conditions.

This behaviour has been recognised by Raman spectroscopy analysis, which revealed the presence of protonated amino-groups of the polymer in the carbonated solution of amino(meth)acrylate polymer (disappearance of the signal at 1392 and 1406 cm-1 and appearance of a wide absorption peak at 1396 cm-1).

The inventive amino(meth)acrylate polymer or copolymer containing carbonated aqueous medium can be easily handled in a similar way like organic solvent solutions. However in this case not the organic solvent is removed but the carbonated water. This means that a dried coating made from the inventive dispersion or solution will consist more or less of the pure amino(meth)acrylate polymer or copolymer since the carbon dioxide is removed with the vapour. This is a striking advantage over the aqueous dispersions known from the state of art, where acids or other excipients always remain with the dried amino(meth)acrylate polymer or copolymer. There is a balance of interaction between the amino(meth) acrylate polymer or copolymer and the carbon dioxide which stays in a stable range for a long period of time, for instance for at least 6 months or more.

DETAILS OF THE INVENTION

The invention refers to an aqueous medium containing an amino(meth)acrylate polymer or copolymer which is not soluble in demineralised water.

Aqueous Phase/Water Content/Solid Content

Aqueous phase in the sense of the invention shall mean an at least predominantly, an essentially or an almost or exactly 100% water containing liquid phase. It is possible, to substitute certain amounts of the water by water soluble fluids like ethanol, acetone or isopropanol. This may be advantageous for the purposes of preventing microbial growth or for the purpose of improving the solution properties (e.g. nebulisation) or the final product properties. In the sense of this invention, the aqueous phase may contain an amount of water soluble or water miscible fluids which is not higher than 40% (weight/weight), more preferred not higher than 30% (w/w), most preferred not higher than 20% (w/w). In any case the resulting solution should not present flammable properties. In the aqueous phase water and water soluble fluids add up to 100%. Most preferred the aqueous phase water consists to 100% of water.

The medium may have a content of an aqueous phase of at least 60%, at least 70, at least 80 or at least 90% and a solid content of up to 40 up to 30, up to 20 or up to 10% by weight. The solid content may be identical with the content of the amino(meth)acrylate polymer or copolymer. However the solid content may also comprise the amino(meth)acrylate polymer or copolymer and further excipients. Liquid, non evaporating excipients with a boiling point above 100° C. shall be regarded as belonging to the solid phase. The aqueous phase and the solids usually or essentially add up to 100%. The presence of carbon dioxide/carbonic acid in the medium or in the aqueous phase can be neglected in the calculation.

Viscosity

The inventive aqueous medium may be characterized in that the viscosity of the medium is 5 to 150, preferably 5 to 40, most preferably from 8 to 15 mPa·s. In this viscosity range the inventive aqueous medium can be used very well for spray coatings or as binding solution or dispersion. Less preferred but also possible, especially when the solution shall be used as a binding agent, the viscosity can be much higher, for instance above 150 up to 10.000 mPa·s. The viscosity may be determined according to ISO 3219: 1993-Plastics-Polymers/Resins in the liquid state or as emulsions or dispersions—Determination of viscosity using a rotational viscometer with defined shear rate.

Carbon Dioxide Content/pH Values

The aqueous phase is charged by a sufficient amount of carbon dioxide that effects the amino(meth)acrylate polymer or copolymer to become soluble or respectively to be present in solute form in the medium, because of the interaction between the carbon dioxide/carbonic acid/hydrogen carbonate in the aqueous phase and the amino groups of the polymer or copolymer. Sufficient shall mean already sufficient or more.

The amount of carbon dioxide which has to be charged to confer the amino(meth)acrylate polymer or copolymer to become soluble in the aqueous phase and the pH window in which the amino(meth)acrylate polymer or copolymer remains stable in the solute state depends on the amino(meth) acrylate polymer or copolymer itself. Factors affecting the solubility properties mainly may be the concentration of the polymer or copolymer and its overall monomer composition, especially the amounts of monomers with amino groups. Other factors like for instance the molecular weight may also have influence on the solubility. However with the knowledge of the present invention a skilled person can easily adapt suitable amounts of carbon dioxide which have to be charged in the aqueous phase to confer different amino(meth)acrylate polymers or copolymers to become soluble and can find out suitable pH windows in which the certain amino(meth)acrylate polymer or copolymer remains stable in the solute state on the basis of the equilibrium described below:

$$CO_2 + H_2O \rightleftharpoons H_2CO_3$$

The hydration equilibrium constant at 25° C. is $K_h = 1.70 \times 10^{-3}$: hence, the majority of the carbon dioxide is not converted into carbonic acid and stays as $CO_2$ molecules. In the absence of a catalyst, the equilibrium is reached quite slowly. The rate constants are $0.039$ $s^{-1}$ for the forward reaction ($CO_2 + H_2O \rightarrow H_2CO_3$) and $23$ $s^{-1}$ for the reverse reaction ($H_2CO_3 \rightarrow CO_2 + H_2O$). Carbonic acid is used in the making of soda (such as sparkling water) etc.

At a given temperature, the composition of a pure carbonic acid solution (or of a pure $CO_2$ solution) is completely determined by the partial pressure of carbon dioxide above the solution. To calculate this composition, account must be taken of the above equilibria between the three different carbonate forms ($H_2CO_3$, $HCO_3^-$ and $CO_3^{2-}$) as well as of the hydration equilibrium between dissolved $CO_2$ and $H_2CO_3$ with constant $K_h = [H_2CO_3]/[CO_2]$ (see above) and of the following equilibrium between the dissolved $CO_2$ and the gaseous $CO_2$ above the solution:

$CO_2(gas) \leftrightarrow CO_2(dissolved)$ with where $k_H = 29.76$ atm/(mol/L) at 25° C. (Henry constant)

The corresponding equilibrium equations together with the relation and the neutrality condition result in six equations for the six unknowns $[CO_2]$, $[H_2CO_3]$, $[H^+]$, $[OH^-]$, $[HCO_3^-]$ and $[CO_3^{2-}]$, showing that the composition of the solution is fully determined by. The equation obtained for $[H^+]$ is a cubic whose numerical solution yields the following values for the pH and the different species concentrations:

| partial pressure $CO_2$ [atm] | pH | $[CO_2]$ (mol/L) | $[H_2CO_3]$ (mol/L) | $[HCO_3^-]$ (mol/L) | $[CO_3^{2-}]$ (mol/L) |
|---|---|---|---|---|---|
| $10^{-8}$ | 7.00 | $3.36 \times 10^{-10}$ | $5.71 \times 10^{-13}$ | $1.42 \times 10^{-9}$ | $7.90 \times 10^{-13}$ |
| $10^{-6}$ | 6.81 | $3.36 \times 10^{-8}$ | $5.71 \times 10^{-11}$ | $9.16 \times 10^{-8}$ | $3.30 \times 10^{-11}$ |
| $10^{-4}$ | 5.92 | $3.36 \times 10^{-6}$ | $5.71 \times 10^{-9}$ | $1.19 \times 10^{-6}$ | $5.57 \times 10^{-11}$ |
| $3.5 \times 10^{-4}$ | 5.65 | $1.18 \times 10^{-5}$ | $2.00 \times 10^{-8}$ | $2.23 \times 10^{-6}$ | $5.60 \times 10^{-11}$ |
| $10^{-3}$ | 5.42 | $3.36 \times 10^{-5}$ | $5.71 \times 10^{-8}$ | $3.78 \times 10^{-6}$ | $5.61 \times 10^{-11}$ |
| $10^{-2}$ | 4.92 | $3.36 \times 10^{-4}$ | $5.71 \times 10^{-7}$ | $1.19 \times 10^{-5}$ | $5.61 \times 10^{-11}$ |
| $10^{-1}$ | 4.42 | $3.36 \times 10^{-3}$ | $5.71 \times 10^{-6}$ | $3.78 \times 10^{-5}$ | $5.61 \times 10^{-11}$ |
| 1 | 3.92 | $3.36 \times 10^{-2}$ | $5.71 \times 10^{-5}$ | $1.20 \times 10^{-4}$ | $5.61 \times 10^{-11}$ |
| 2.5 | 3.72 | $8.40 \times 10^{-2}$ | $1.43 \times 10^{-4}$ | $1.89 \times 10^{-4}$ | $5.61 \times 10^{-11}$ |
| 10 | 3.42 | 0.336 | $5.71 \times 10^{-4}$ | $3.78 \times 10^{-4}$ | $5.61 \times 10^{-11}$ |

We see that in the total range of pressure, the pH is always largely lower than $pKa_2$ so that the $CO_3^{2-}$ concentration is always negligible with respect to $HCO_3^-$ concentration. In fact $CO_3^{2-}$ plays no quantitative role in the present calculation (see remark below).

For vanishing, the pH is close to the one of pure water (pH=7) and the dissolved carbon is essentially in the $HCO_3^-$ form.

For normal atmospheric conditions, we get a slightly acid solution (pH=5.7) and the dissolved carbon is now essentially in the $CO_2$ form. From this pressure on,

[OH⁻] becomes also negligible so that the ionized part of the solution is now an equimolar mixture of H⁺ and $HCO_3^-$.

For a $CO_2$ pressure typical of the one in soda drink bottles (ca. 2.5 atm), we get a relatively acid medium (pH=3.7) with a high concentration of dissolved $CO_2$. These features contribute to the sour and sparkling taste of these drinks.

Between 2.5 and 10 atm, the pH crosses the $pKa_1$ value (3.60) giving a dominant $H_2CO_3$ concentration (with respect to $HCO_3^-$) at high pressures.

A sufficient amount of carbon dioxide that effects the amino(meth)acrylate polymer or copolymer to be become soluble or respectively to be present in solute form in the medium can be defined to be at least enough to convert the amino(meth)acrylate polymer or copolymer when it is present in water from the dispersed state to a state of solubility. As a rough rule an aqueous medium which has been charged with carbon dioxide at 25° C. under normal pressure conditions (1 bar) contains a sufficient amount of carbonic acid to make the dispersed polymer soluble. The state of solubility is reached when the turbid dispersion has become clear and is stable within the range from pH 5.5 and pH 8.0, from pH 6.0 and pH 7.5 from pH 6.7 and pH 7.4 from pH 6.8 and pH 7.3, at room temperature (ca. 25° C.) and normal pressure (1 bar).

As a rough rule demineralized water which has been charged with carbon dioxide at 25° C. under normal pressure conditions contains a sufficient amount of carbonic acid when its pH is between 4.0 and 5.5. In this state the water should be sufficiently charged with carbon dioxide to convert at least 25% by weight of an amino(meth)acrylate polymer or copolymer which is composed of polymerized units of 25% by weight of methyl methacrylate, 25% by weight of butyl methacrylate and 50% by weight of dimethylaminoethyl methacrylate (EUDRAGIT® E) to become soluble, when the copolymer is dissolved into the water.

Under pressure, for instance 2 to 10 bar, even more carbon dioxide may be charged into the water so that pH values around pH 3.5 can be reached. In this state even higher amounts up to 40% of an amino(meth)acrylate polymer or copolymer may be converted to become solute in the water.

When the amino(meth)acrylate polymer or copolymer is stirred in to the charged water and becomes solute the pH increases and can be in the range of for instance from 5.5 to 8.0.

A sufficient amount of carbon dioxide in the water can be for instance present when an amino(meth)acrylate polymer or copolymer which is composed of polymerized units of 20-30% by weight of methyl methacrylate, 20-30% by weight of butyl methacrylate and 60-40% by weight of dimethylaminoethyl methacrylate (EUDRAGIT® E-type), preferably an amino(meth)acrylate polymer or copolymer which is composed of polymerized units of 25% by weight of methyl methacrylate, 25% by weight of butyl methacrylate and 50% by weight of dimethylaminoethyl methacrylate (EUDRAGIT® E), when it is present in an amount of 12 to 22, preferably 15% by weight in the medium, and the medium is clear from pH 6.7 to 7.3, preferably from pH 6.8 to 7.2.

When the amount of carbon dioxide in the water decreases to a critical value by the increasing emission of carbon dioxide to the surrounding air, it is supposed that the amount of neutralized amino groups in the amino(meth)acrylate polymer or copolymer becomes too low to keep the amino(meth)acrylate polymer or copolymer in solution. This can be observed and characterized indirectly by an increase of the pH of the medium over a critical value. In a specific case the critical pH range of the medium may be between pH 7.2 and 7.3 When the pH of the medium exceeds these values, the medium becomes more and more turbid and the amino(meth)acrylate polymer or copolymer becomes insoluble and precipitates.

Amino(Meth)Acrylate Polymer or Copolymer

The carbonated aqueous medium may contain up to 40%, up to 30%, up to 25% by weight of an amino(meth)acrylate polymer or copolymer. From a practical approach a polymer or copolymer content of 12 to 22% by weight is quite suitable to work with, especially for spray coating.

The amino(meth)acrylate polymer or copolymer is preferably a copolymer composed of polymerized units of $C_1$- to $C_4$-alkyl esters of acrylic or methacrylic acid and of alkyl (meth)acrylate monomers with a tertiary amino group in the alkyl radical.

Carbonated aqueous medium preferably comprises or essentially contains or contains an amino(meth)acrylate copolymer is composed of polymerized units of 30 to 80% by weight of $C_1$- to $C_4$-alkyl esters of acrylic or of methacrylic acid and 70 to 20% by weight of alkyl(meth)acrylate monomers having a tertiary amino group in the alkyl radical.

Carbonated aqueous medium preferably comprises or essentially contains or contains an amino(meth)acrylate copolymer is composed of polymerized units of 20-30% by weight of methyl methacrylate, 20-30% by weight of butyl methacrylate and 60-40% by weight of dimethylaminoethyl methacrylate.

Amino (Meth)Acrylat Copolymer

The copolymer component (a) may be a so called "amino methacrylate copolymer (USP/NF)", "basic butylated methacrylate copolymer (Ph. Eur)" or "aminoalkyl Methacrylate Copolymer E (JPE)" which are of the EUDRAGIT® E type.

The amino(meth)acrylate polymer or copolymer is preferably a copolymer of the EUDRAGIT® E type. Suitable (meth)acrylate copolymers are known, for example, from EP 0 058 765 B1.

The amino (meth)acrylate copolymer may be composed, for example, of 30 to 80% by weight of free-radically polymerized $C_1$- to $C_4$-alkyl esters of acrylic acid or of methacrylic acid, and 70 to 20% by weight of (meth)acrylate monomers having a tertiary amino group in the alkyl radical.

Suitable monomers with functional tertiary amino groups are detailed in U.S. Pat. No. 4,705,695, column 3 line 64 to column 4 line 13. Mention should be made in particular of dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethyl)propyl methacrylate, (3-diethylamino-2,2-dimethyl)propyl acrylate, diethylamino-2,2-dimethyl)propyl methacrylate and diethylaminoethyl methacrylate.

Particular preference is given to dimethylaminoethyl methacrylate.

The content of the monomers with tertiary amino groups in the copolymer may advantageously be between 20 and 70% by weight, preferably between 40 and 60% by weight. The proportion of the $C_1$- to $C_4$-alkyl esters of acrylic acid or methacrylic acid is 70-30% by weight. Mention should be made of methyl methacrylate, ethyl methacrylate, butyl methacrylate, methyl acrylate, ethyl acrylate and butyl acrylate.

A suitable amino (meth)acrylate copolymer may be polymerized out of, for example, from 20-30% by weight of methyl methacrylate, 20-30% by weight of butyl methacrylate and 60-40% by weight of dimethylaminoethyl methacrylate.

A specifically suitable commercial amino (meth)acrylate copolymer is, for example, formed from 25% by weight of methyl methacrylate, 25% by weight of butyl methacrylate and 50% by weight of dimethylaminoethyl methacrylate (EUDRAGIT® E100 or EUDRAGIT® E PO (powder form)). EUDRAGIT® E100 and EUDRAGIT® E PO are water-soluble below approx. pH 5.0 and are thus also gastric juice-soluble.

Excipients

The medium may contain water, carbon dioxide (carbon dioxide/carbonic acid/hydrogen carbonate) and the amino (meth)acrylate polymer or copolymer alone or may contain further excipients which are commonly used in the field of pharmacy or nutraceuticals or cosmetics. These kinds of excipients are well known to a skilled person but not critical for the invention.

It is self evident that excipients that would chemically interact with the amino(meth)acrylate polymer or copolymer because of their chemical nature or because of their concentration and thus would impede the solubility of the amino (meth)acrylate polymer or copolymer shall be excluded. Such unwanted chemical interactions could further hinder the taste masking or the moisture preventing effect. Of course an amino(meth)acrylate polymer or copolymer is not an excipient in the sense of the invention. Of course carbon dioxide is not an excipient in the sense of the invention. However polymers or copolymers which are not amino(meth)acrylate polymers or copolymers may be used as excipients as long as they are not critical for the invention in the above discussed sense. Anionic polymers or anionic (meth)acrylate copolymers which could interact with the amino(meth)acrylate polymers or copolymers may be excluded.

The carbonated aqueous medium is characterized in that excipients which are commonly used in pharmacy, nutraceuticals or cosmetics may be contained.

Preferably the excipients are selected from the classes of antioxidants, brighteners, flavouring agents, flow aids, fragrances, glidants (release agents), penetration-promoting agents, pigments, plasticizers, polymers, pore-forming agents or stabilizers or combinations thereof.

The term pharmaceutical, nutraceutical or cosmetical excipients is well known to the skilled person. Many excipients are customary used in pharmacy but also in the field of nutraceuticals or cosmetics, occasionally also they are referred as customary additives. It is, of course, always necessary for all the excipients or customary additives employed to be toxicologically acceptable and usable in particular in food or in medicaments without a risk for customers or patients.

Although the requirements are usually higher in the pharmaceutical field there is a widely overlap of excipients used for pharmaceutical purposes and those used for nutraceutically or cosmetically purposes. Usually all pharmaceutical excipients may be used for nutraceutically or cosmetically purposes and at least a large number of nutraceutical excipients are allowed to be used for pharmaceutical purposes as well. Excipients may be are added to the formulation of the invention, preferably during production of the granules or the mixing of the powders.

Pharmaceutical, nutraceutical or cosmetical excipients may be contained for practical reasons, for instance to avoid stickiness or to add a colour. However these excipients usually do not contribute or do show any or almost no effect on the invention itself as claimed here. They may be used as processing adjuvants and are intended to ensure a reliable and reproducible preparation process as well as good long-term storage stability, or they achieve additional advantageous properties in the pharmaceutical form. They are added to the polymer formulations before processing and can influence the permeability of the coatings. This property can be used if necessary as an additional control parameter. Of course all kind of excipients used must of course be toxicologically safe and to be used in cosmetics, nutraceuticals or pharmaceuticals without risk for customers or patients.

Glidants/Release Agents:

Release agents usually have lipophilic properties and are usually added to spray suspensions. They prevent agglomeration of cores during film formation. There are preferably used talc, Mg- or Ca-stearate, ground silica, fused silica, kaolin or nonionic emulsifiers with an HLB value of between 3 and 8. Preferred is glycerol monostearate (GMS). If the excipient is a glidant it may be contained at a concentration of 1 to 100, preferably 5 to 15% by weight based on the amino(meth)acrylate polymer or copolymer.

Pigments:

Only rarely is the pigment added in soluble form. As a rule, aluminium oxide or iron oxide pigments are used in dispersed form. Titanium dioxide is used as a whitening pigment. If the excipient is a pigment it may be contained at a concentration of up to 200% by weight based on the amino(meth)acrylate polymer or copolymer.

Plasticizers

Plasticizers achieve through physical interaction with the polymers of the polymer mixture a reduction in the glass transition temperature and promote film formation, depending on the added amount. Suitable substances usually have a molecular weight of between 100 and 20 000 and comprise one or more hydrophilic groups in the molecule, e.g. hydroxyl, ester or amino groups.

Examples of suitable plasticizers are alkyl citrates, glycerol esters, alkyl phthalates, alkyl sebacates, sucrose esters, sorbitan esters, diethyl sebacate, dibutyl sebacate and polyethylene glycols 200 to 12 000. Preferred plasticizers are triethyl citrate (TEC), acetyl triethyl citrate (ATEC), diethyl sebacate and dibutyl sebacate (DBS). Mention should additionally be made of esters which are usually liquid at room temperature, such as citrates, phthalates, sebacates or castor oil. Esters of citric acid and sebacinic acid are preferably used. The addition of $C_{12}$-$C_{18}$ monocarboxylic acid, especially stearic acid, at a concentration of 5 to 25, preferably 5 to 15% by weight based on the amino(meth)acrylate polymer or copolymer, seems to decrease the water vapor permeability.

Addition of the plasticizers to the formulation can be carried out in a known manner, directly, in aqueous solution or after thermal pre-treatment of the mixture. It is also possible to employ mixtures of plasticizers. If the excipient is a plasticizer it may be contained at a concentration of up to 50, preferably 2 to 25% by weight based on the amino(meth)acrylate polymer or copolymer.

Most preferably triethylcitrat, dibutylsebacat and/or stearic acid are contained.

Plasticizers like for instance triethylcitrat, dibutylsebacat may be contained in comparably low amounts of 0.5 to 10 or 1 to 5% by weight.

Storage

To avoid risk that the solute amino(meth)acrylate polymer or copolymer becomes insoluble again and precipitates, one should prevent the emission or disappearance of carbon dioxide from the aqueous medium. Thus the carbonated aqueous medium may be preferably stored in open or closed containers under carbon dioxide atmosphere. Preferred containers are made of polymeric materials or metals to avoid carbon dioxide diffusion or leakage. Preferred containers are made from polyethylene, polypropylene or polyethylene terephthalate. In such containers the inventive aqueous medium may be stored in stable form, without precipitation of the amino (meth)acrylate polymer or copolymer, for up to several months or even more. If a container is once opened, the contained medium can be usually used in stable form for further coating or binding processes for at least several hours. If a rest of the medium remains in the container it recommended to add carbon dioxide gas before it is closed and stored again.

Process

The invention discloses a process for preparing a carbonated aqueous medium by charging aqueous phase with carbonic acid and dissolving therein an amino(meth)acrylate polymer or copolymer which is not soluble in pure water but soluble in the carbonic acid charged water.

The process may be characterized in that the aqueous phase is charged with carbonic acid up to the saturation point by contacting carbonic acid in the gas form with the water at normal pressure conditions or under pressure of up to 10, preferably 2 to 8 bar. Suitable processing temperatures may be in the range of 10 to 60° C.

The Process may be characterized in that the aqueous phase is charged with carbonic acid up to the saturation point by contacting carbonic acid in the gas form with the aqueous phase in a pressure reactor under pressure of 100 to 1000 mbar, decreasing the pressure to normal conditions and subsequently dissolving the amino(meth)acrylate polymer or copolymer in the carbonated aqueous phase under stirring until the polymer or copolymer is dissolved completely.

Use/Applications

The invention discloses the use of the aqueous medium containing an amino(meth)acrylate polymer or copolymer as a coating or binding solution for the spray coating or binding of pharmaceutical compositions, preferably active ingredient containing pharmaceutical compositions in the form of pellets, granules, minitablets, tablets or capsules or nutraceutical compositions or cosmetical compositions. The use as a coating solution shall include the use as a subcoat or a topcoat in combination with other coatings.

Nutraceuticals

Nutraceuticals can be defined as extracts of foods claimed to have medical effects on human health. The nutraceutical is usual contained in a medical format such as capsule, tablet or powder in a prescribed dose. Examples for nutraceuticals are resveratrol from grape products as an antioxidant, soluble dietary fiber products, such as psyllium seed husk for reducing hypercholesterolemia, broccoli (sulphane) as a cancer preservative, and soy or clover (isoflavonoids) to improve arterial health. Other nutraceuticals examples are flavonoids, antioxidants, alpha-linoleic acid from flax seed, beta-carotene from marigold petals or antocyanins from berries. Sometimes the expression neutraceuticals is used as synonym for nutraceuticals.

Cosmetics

Cosmetics are substances used to enhance or protect the appearance or odor of the human body. Typical cosmetical active ingredients may comprise vitamins, phytochemicals, enzymes, antioxidants, and essential oils. Cosmetics may include skin-care creams, lotions, powders, perfumes, lipsticks, fingernail and toe nail polish, eye and facial makeup, permanent waves, colored contact lenses, hair colors, hair sprays and gels, deodorants, baby products, bath oils, bubble baths, bath salts, butters and many other types of products. Their use is widespread, especially among women but also by men. A subset of cosmetics is called "make-up," which refers primarily to colored products intended to alter the user's appearance. Many manufacturers distinguish between decorative cosmetics and care cosmetics. The term cosmetics shall include topically applied forms such as so called cosmeceuticals as well as orally ingested forms such as so called nutricosmetics.

EXAMPLES

Copolymers Used: EUDRAGIT® E and EUDRAGIT® E PO

EUDRAGIT® E is a copolymer composed of 25% by weight of methyl methacrylate, 25% by weight of butyl methacrylate and 50% by weight of dimethylaminoethyl methacrylate. EUDRAGIT® E is in a granulate form. EUDRAGIT® E PO is in a powder form.

Example 1(E1)

Small Laboratory Scale Manufacturing of a Carbonated EUDRAGIT® E Solution at Normal Conditions In a 1 liter PE-beaker 465 g water were poured. After dissolving 15 g of TEC in the water at 1000 Rpm using a conventional stirrer with dissolver plate (diameter: 5 cm). 75 g EUDRAGIT® E 100 granules (1-3 mm in diameter) were dispersed for 5 min at 22,000 rpm using an Ultra Turrax. Then 3.5 g simethicon dispersion (5%) was added and finally water ad 600 g. Under stirring at 500 rpm using the conventional stirrer with dissolver plate, the dispersion was carbonized 24 h above the liquid at normal conditions, temperature (25° C.) and pressure (1013 mbar). A weak turbid solution was obtained. Viscosity of the 12.5% EUDRAGIT® E containing solution (amount before carbonization) was 5.6 mPa*s at 25° C. The pH of the fresh prepared carbonized solution was 6.75. The solution was filled in a 1 liter polyethylene terephthalate (PET) bottle with a polyethylene closure.

Example 2(E2)

Medium Scale (20%-wt.) Manufacturing of a Carbonated EUDRAGIT® E Solution Under Pressure 2.4 kg water was poured into a 5 liter beaker. Then 600 g EUDRAGIT® E PO were dispersed during 15 min at 2000 rpm using a conventional stirrer with dissolver plate (diameter: 5 cm). 3 kg of the suspension have been poured into a 6.4 liter stainless steel reactor with $CO_2$ supply. The reactor was closed and the propeller stirrer was set at ca. 150 rpm under a 5.0 bar $CO_2$ pressure. The rotary speed was increased up to ca. 350 rpm after 15 minutes. During the whole process time (ca. 7 h) the $CO_2$ pressure was adjusted every half an hour to ca. 5 bar (min. pressure was 3.6 bar). The final product was a clear, slight viscous yellowish solution. Subsequently, the pressure was reduced to normal pressure (ca. 2 hours), the product was poured in 1 liter PET bottles. Final yield was 2800 g, of a 20% by weight EUDRAGIT® E solution. The pH value was 6.8 and the viscosity was 14 mPa*s at 25° C.

Example 3(E3)

Medium Scale (30%-wt.) Manufacturing of a Carbonated EUDRAGIT® E Solution Under Pressure 2.8 kg water were poured into a 6.4 liter reactor with $CO_2$ supply. Then 1.2 kg EUDRAGIT® E 100 were added under stirring at 300 rpm with a propeller stirrer (7 cm in diameter). The reactor was closed and the propeller stirrer was set to ca. 550 rpm and $CO_2$ pressure was set to 5.0 bar. During the whole process time of 6 h at 25° C. the $CO_2$ pressure was adjusted every half an hour to 5 bar (min. pressure was 3.4 bar). Subsequently, the pressure was reduced to normal pressure (ca . . . 1 hour), the product was poured in 1 liter PET bottles. The bottles were closed immediately because of foam forming. Final yield was 3.5 kg. The viscosity was 138 mPa*s at 23° C.

Example 4(E4)

Comparison of the pH Values of the EUDRAGIT® E Carbonate Solutions of E2 and E3

Solutions of E2 and E3 were filled into 30 ml glass bottles closed with screwing cap. A 10% w/w EUDRAGIT® E carbonate solution was obtained by dilution of the 20% E2 solution with water. At each measurement time the sampled bottles were opened for not more than 3 min and the pH-electrode was dipped into the uncovered solution under moderate stirring. During storage in the refrigerator at 2-8° C. no precipitation was observed. However, precipitation of EUDRAGIT® E particles was observed after pH reached values in the region of 7.3-7.5 or more. Every time the sample bottles were opened for measurements, a slight overpressure could be organoleptic recognized (a sound like the opening of a sparkling water bottle) indicating a small release of $CO_2$ from the solution. The results are described in table 1. The higher the concentration of the polymer, the lower was the pH at which the first indication of precipitation of the polymer could be recognized.

TABLE 1

| | Example | | |
|---|---|---|---|
| | E2 diluted | E2 | E3 |
| | Concentration EUDRAGIT ® E [wt.-%] | | |
| | 10 | 20 | 30 |
| | stored at [° C.] | | |
| | 2-8 | | |
| Time [days] | pH at 21-24° C. | | |
| 0 | 6.84 | 6.95 | 7.08 |
| 1 | 6.84 | 6.94 | 7.09 |
| 2 | 6.85 | 6.93 | 7.10 |
| 3 | 6.87 | 6.95 | 7.11 |
| 6 | 6.85 | 6.94 | 7.07 |
| 7 | 6.83 | 6.94 | 7.04 |
| 8 | 6.94 | 6.91 | |
| 10 | | | |
| 13 | 6.92 | 6.96 | 7.09 |
| 14 | 6.94 | 6.98 | 7.05 |
| 15 | 6.98 | 7.00 | 7.12 |
| 16 | 7.00 | 7.02 | 7.11 |
| 17 | 7.02 | 7.04 | 7.10 |
| 19 | | | |
| 21 | 7.13 | 7.08 | 7.16 |
| 22 | 7.12 | 7.07 | 7.13 |
| 23 | 7.17 | 7.10 | 7.19 |
| 24 | 7.10 | 7.06 | 7.16 |
| 27 | 7.16 | 7.15 | 7.19 |
| 28 | 7.30 | 7.23 | 7.25 |
| 29 | 7.33 | 7.30 | 7.28* |
| 34 | | 7.32 | 7.25* |
| 35 | 7.35 | 7.30* | 7.24* |
| 36 | 7.40 | 7.35* | 7.20* |
| 37 | 7.43* | 7.37* | 7.25* |
| 38 | 7.45* | 7.38* | 7.27* |
| 45 | | | |
| total time, open bottle, min | 69 | 72 | 69 |
| Initial pH | 6.84 | 6.95 | 7.08 |
| Final pH | 7.45 | 7.38 | 7.27 |

*= Dry particles were found in the solution, most of the solution was still remaining clear

Example 5(E5)

Practical Approach: Measurement of Viscosity and pH of EUDRAGIT® E Carbonate Solutions in Open Container Under practical conditions for instance for spray coating application it is common practice that the spraying solution is soaked from open containers usually from bottles for a period of about 2 to 4 hours. Thus it should be tested if an EUDRAGIT® E carbonate solution would remain stable without signs of precipitation in an open bottle container for 4 hours.

200 g of the 20% (w/w) EUDRAGIT® E carbonate solution of Example 2, were poured into a 250 ml glass bottle that was kept opened, as usually occurs during coating trials. A pH electrode and a temperature sensor, connected to a pH meter were inserted into the liquid and the pH values were measured every 1 hour for 4 h under stirring, using a stirrer provided with a dissolver plate (diameter 3 cm) at ca. 540 rpm (500-600 rpm) and at a temperature of 23° C. In parallel 20 ml samples were collected and analyzed using a rotary viscosimeter at 25° C. and a shear rate of 100 $s^{-1}$. The Viscosity of the 20% EUDRAGIT® E carbonate solution tends to decrease by evaporation of carbon dioxide resulting to higher pH values. However no signs of precipitation could be recognized which is coincident with the pH value of 7.12 after 4 hours which is below the expected precipitation point around 7.3. The results are described in table 2.

TABLE 2

| Time, min | 0 | 60 | 120 | 180 | 240 |
|---|---|---|---|---|---|
| viscosity, mPa · s | 11.80 | 10.21 | 8.69 | 8.43 | 8.06 |
| pH value | 6.80 | 6.91 | 6.97 | 7.04 | 7.12 |

Comparison Example 6(C6)

Manufacturing of an Organic EUDRAGIT® E 100 Solution 3.400 g Acetone, 5,100 g Isopropyl alcohol and 250 g water were poured in a 15 liter stainless steel vessel and stirred at room temperature using conventional propeller stirrer (diameter 8 cm). 1,250 g EUDRAGIT® E 100 were added in portions into the solvent mixture. The intensity of stirring was adjusted to avoid sedimentation of not dissolved granules. After about 45 minutes the solid substance turned into a clear yellowish solution. Polymer content was 12.5%. Viscosity was 12 mPa*s (25° C.).

Comparison Example 7(C7)

Manufacturing of an Aqueous Dispersion Containing EUDRAGIT® EPO with Stearic Acid and Sodium Laurylsulfate (so Called Standard Formulation)

1416 g water were poured into a 3 liter beaker and by setting the stirring speed at ca. 5900 rpm using a rotor-stator dispersing unit, 20 g SDS were added and thereafter 30 g stearic acid. After 1 minute stirring, 200 g E PO were poured little by little letting the dispersion mix properly: the speed was increased at first up to ca. 6500 rpm until reaching ca. 7400 rpm. Once the dispersion looked homogeneous, it was stirred for further 30 minutes: as soon as foam formation started to increase, the speed was reduced to avoid too much foam. The dispersion was left standing until foam disappeared (ca. 4 hours). Solid content of the dispersion was 15%, yield was 100%, pH of the solution was 9.3, and the viscosity of the yellowish/greenish opalescent dispersion was 10 mPa*s (25° C.).

Example 8(E8)

Comparison of the Water Vapor Permeability of Films Made From the Solutions of E2 and C6

56.25 g of the EUDRAGIT® carbonate solution of E2 were mixed 1.13 g water and 2.5%-by weight (0.28 g) triethyl citrate (TEC) based on polymer under stirring with a conventional stirrer at 200 rpm for 25 min. A clear yellowish solution with a pH value of 6.8 was obtained.

2.5%-by weight (0.313 g) TEC based on polymer was dissolved in 100 g organic solution of C6. Both solutions were stable for several weeks without precipitates forming and formed transparent flexible films after drying. Water vapor permeability values of both formulations were measured and found to be comparable (E2: 342 +/−22 and C6: 324 +/−23 g/m$^2$/d).

The water vapor permeability of polymers films can be analysed by measuring the diffusion of the water vapor through the films in the style of the gravimetric water vapor permeability method described in DIN 53122. The selected humidity at 23° C. was 85% relative humidity analog to DIN 53122, climate D as described in chapter 8.2.

Example 9(E9)

Influence of the Addition of Stearic Acid on the Water Vapor Permeability of Films Made From EUDRAGIT® E Carbonate Solutions of E2

25.13 g water was added to 56.25 g of EUDRAGIT® carbonate solution of E2. Then 1.13 g stearic acid (10%-by weight based on polymer) were added and dissolved under stirring for ca. 1 h at 900 rpm, i.e. until a clear slightly yellowish solution with a pH value of 7.1 was observed and formed a transparent flexible film after drying. In comparison to the films obtained in E8, the water vapor permeability value of the dry film decreased to 227 +/−12 g/m$^2$/d.

Comparison Example 10(C10)

Water Vapor Permeability of Films Made from the EUDRAGIT® E Dispersion of C7 (Standard Formulation) with the Addition of TEC A dispersion manufactured as described in C7 was added with 2.5% TEC based on polymer. 30 g were dried on a glass plate at room temperature. After drying overnight an opalescent flexible film was obtained. The water vapor permeability of the film was 229 +/−24 g/m2/d.

Example 11(E 11)

Test for Sedimentation and Redispersion in the Presence of 10 wt.-% of the Glidant Glycerol Monostearate (GMS)

The addition of glidants like GMS is important under practical aspects to avoid stickiness. However it is known that glidants may cause unwanted side effects like phase separation followed by sedimentation or floating. These unwanted effects may be more or less harmless if the sediment can be redispersed. Thus the EUDRAGIT® carbonate solution of E2 should be tested for stability against sedimentation in the presence of GMS and if sedimentation should occur whether such a sediment can be redispersed.

20.79 g water and 0.15 g Tween® 80 (4 wt. % based on polymer) were dissolved into a 250 ml bottle (A), the top was covered with aluminium foil and the solution was heated up to 70° C. under magnetic stirring (600 rpm). Subsequently 0.38 g GMS (10 wt.-% based on polymer) were added and the stirring speed was increased up to 900 rpm while the dispersion cooled down slowly. 37.5 g EUDRAGIT® E carbonate solution, as manufactured in E2, were poured into another bottle (B) together with 0.19 g TEC (2.5 wt.-% based on polymer) and, once closed, stirred for 10 min at 600 rpm. Then 0.75g stearic acid (10 wt.-% based on polymer) were added under stirring for ca. 1 h at 900 rpm, i.e. until a clear yellowish solution was observed.

As soon as the temperature of the glycerol monostearate/ Tween® 80 containing dispersion from bottle A was between 20 and 30° C., it was poured into the bottle B with EUDRAGIT® E hydrogen carbonate solution and left stirring for 1 hour at 700 rpm. The pH value of the white turbid fine dispersion, obtained was 6.93.

After 1 week the dispersion (with 10% glycerol monostearate) showed a slight phase separation, but no sedimentation. After redispersion by simple conversion of the bottle the slight phase separation disappeared.

Example 12(E 12)

Test for Sedimentation and Redispersion in the Presence of 5 wt.-% of the Glidant Glycerol Monostearate (GMS)

E12 was carried out in the same manner as in example E11 but with 5%.-wt GMS. After 24 hours the dispersion (with 5%.-wt glycerol monostearate) showed a phase separation with slight sedimentation. After redispersion by multiple conversion of the bottle the phase separation and sedimentation disappeared.

Example 13(E 13)

Coating Trial with EUDRAGIT® E Carbonate Solution Containing GMS and TEC on Bitter Tasting Quinidine Sulfate Pellets A spray coating dispersion, containing EUDRAGIT® E carbonate solution, GMS and TEC, has been manufactured as described in example E 11 but without stearic acid and Tween® 80. 100 g quinidine sulfate pellets 1 mm to 1.2 mm in diameter were sprayed, applying 7.5% EUDRAGIT® E (based on dry substance) using a conventional fluid bed coating system with bottom spray equipment. The parameters are listed in table 3. The final weight of free-flowing pellets obtained was 106.65 g corresponding to 98.7% of the theoretical yield. As a result a smooth coating was obtained in the absence of stearic acid and Tween® 80. The taste of the coated pellets was neutral.

TABLE 3

| | |
|---|---|
| batch size [g] | 100 |
| air flow [m³/h] | 15 |
| atomizing pressure [bar] | 0.5 |
| micro climate [bar] | 0.4 |
| spraying time [min] | 25 |
| inlet air temperature [° C.] | 41-47 |
| product temperature [° C.] | 26-32 |
| exhaust air temperature [° C.] | 28-29 |
| exhaust air humidity [%] | 18-50 |
| pump scale [rpm] | 2.5-6.5 |
| spray rate [g/min] | 1.0-2.7 |

Comparison Example 14(C14)

Manufacturing of an EUDRAGIT® E Solution Containing EUDRAGIT® EPO Hydrochloric Acid and TEC 50 g water was poured into a beaker, and 15 g EUDRAGIT® E PO were added, while stirring with a propeller stirrer at 800 rpm. During stirring, 0.375 g TEC (2.5% based on polymer) was added. As soon as the dispersion looked homogeneous, 20 g hydrochloric acid (HCl) 1 molar were added and all was left stirring for further 40 minutes at the same speed. At the end a slight yellowish turbid solution was observed. The pH of the solution was 6.7 and further 6 g HCl 1M were added for further neutralization of EUDRAGIT® E; then 10 g water were poured as well to reach the 100 g solution amount. After 3 min stirring at 600 rpm the final pH of the yellowish and clear solution, obtained was 6.6. Films made from this solution were clear and flexible and again soluble in distilled water. The film material had unpleasant bitter like taste after 1 minute.

Example E15

Manufacturing of an Film From EUDRAGIT® E Carbonate 30 g EUDRAGIT® E hydrogen carbonate as manufactured in example E2 with addition of 2.5% TEC. The solution was dried on a glass plate overnight at room temperature. The film was clear, flexible and insoluble in distilled water. The taste of the film material after drying had a neutral taste.

Example E16

Comparison of the Theophylline Release at pH 6.8 According to Pharmacopeia of Theopylline Pellets Coated with Dispersions/Solutions of EUDRAGIT® E From the Examples E2, E9, C6 and C7

Pellets were coated with dispersions/solutions of EUDRAGIT® E from the examples E2, E9, C6 and C7 as described in example 13. The dissolution test of the different EUDRAGIT® E coated theophylline pellets was carried out in a dissolution test device according to USP apparatus 2. 150 mg of each sample were added into a 900 ml glass vessel containing 700 ml 0.1 M HCl. The liquid was stirred at a paddle speed of 150 rpm and at 37° C. The dissolution in buffer pH 6.8, n=3, was analyzed with the same device conditions, too. Collected samples were analyzed using online-UV-photometry at 270 nm. All pellet formulations showed 100% release of theophylline in 0.1 M HCl at 37° C. after a maximum of 10 minutes.

The results of the theophylline release in buffer pH 6.8 are described in table 4. E9 and C7 showed a similar fast release behaviour (see for instance the 60 min values). This is remarkable because the water vapor permeability value of the dry film of E9 was only 227 g/m²/d. Thus the addition of stearic acid to the EUDRAGIT® E carbonate solution combines fast active ingredient release and low water vapor permeability. C6 (organic solution) showed the slowest release. E2 was in between.

TABLE 4

Spray coating trials on theophylline pellets

| | Release of Theophylline at pH 6.8, % w/w | | | | | |
|---|---|---|---|---|---|---|
| Example/Excipient | 30 min | 60 min | 90 min | 120 min | 180 min | 240 min |
| E2: EUDRAGIT ® E carbonate | 6.5 | 37.7 | 71.2 | 93.2 | 98.4 | 100.3 |
| C7: Standard formulation EUDRAGIT ® EPO, STA 15%, SDS 10% | 42.6 | 89.9 | 97.3 | 98.6 | 99.3 | 99.5 |
| E9: EUDRAGIT ® E carbonate, STA 10% | 45.9 | 78.1 | 94.0 | 99.3 | 99.4 | 99.6 |
| C6: EUDRAGIT ® E organic solution | 0.75 | 4.7 | 26.7 | 59.3 | 97.1 | 99.9 |

Legend:
STA = stearic acid,
SDS = sodium lauryl sulfate,
% = % by weight

The invention claimed is:
1. An aqueous medium, comprising:
an amino(meth)acrylate polymer or copolymer which is not soluble in demineralised water, comprising polymerized units of 20-30% by weight of methyl methacrylate, 20-30% by weight of butyl methacrylate, and 60-40% by weight of dimethylaminoethyl methacrylate,
wherein the medium has a content of an aqueous phase of at least 60% by weight and a content of 10 to 22% by weight of the amino(meth)acrylate polymer or copolymer, and
wherein the aqueous phase is charged by a sufficient amount of carbon dioxide that effects the amino(meth)acrylate polymer or copolymer present in solute form in the medium.

2. The aqueous medium of claim 1, wherein the medium has a pH of 6.7 to 7.4.

3. The aqueous medium of claim 1, wherein the amino (meth)acrylate polymer or copolymer content is 10 to 20% by weight.

4. The aqueous medium of claim 1, wherein the medium has a viscosity of 5 to 150 mPa·s.

5. The aqueous medium of claim 1, further comprising a pharmaceutical or a nutraceutical excipient.

6. The aqueous medium of claim 5, wherein the pharmaceutical or nutraceutical excipient is at least one selected from the group consisting of an antioxidant, a brightener, a colorant, a flavouring agent, a flow aid, a fragrance, a glidant, a penetration-promoting agent, a pigment, a plasticizer, a pore-forming agent, and a stabilizer.

7. The aqueous medium of claim 6, further comprising at least one selected from the group consisting of triethylcitrate and stearic acid.

8. The aqueous medium of claim 1, wherein the medium is comprised in a container comprising a carbon dioxide atmosphere.

9. The aqueous medium of claim 1, wherein the medium is comprised in a container comprising polyethylene or polyethylene terephthalate.

10. A process for preparing the aqueous medium of claim 1, the process comprising: charging the aqueous phase with carbonic acid, to obtain a carbonic acid charged aqueous phase; and dissolving the amino(meth)acrylate polymer or copolymer which is not soluble in pure water but soluble in the carbonic acid charged aqueous phase.

11. The process of claim 10, further comprising
charging the aqueous phase with carbonic acid up to a saturation point by contacting carbonic acid in a gas form with the aqueous phase at 25° C. and normal pressure conditions or under a pressure of up to 10 bar.

12. The process of claim 10, further comprising,
charging the aqueous phase with carbonic acid up to a saturation point by contacting carbonic acid in a gas form with the aqueous phase in a pressure reactor at a pressure of 100 to 1000 mbar,
decreasing the pressure to normal conditions, and subsequently
dissolving and stirring the amino(meth)acrylate polymer or copolymer in the carbonated aqueous phase until the polymer or copolymer is dissolved completely.

13. A process of coating a pharmaceutical, nutraceutical, or cosmetical composition, the process comprising:
contacting the aqueous medium of claim 1 with a pharmaceutical, nutraceutical, or cosmetical composition,
wherein the pharmaceutical, nutraceutical, or cosmetical composition is in the form of a pellet, a granule, a minitablet, a tablet, or a capsule.

14. A process of binding a pharmaceutical, nutraceutical, or cosmetical composition, the process comprising:
contacting a binding solution comprising the aqueous medium of claim 1 with a pharmaceutical, nutraceutical, or cosmetical composition,
wherein the pharmaceutical, nutraceutical, or cosmetical composition is in the form of a pellet, a granule, a minitablet, a tablet, or a capsule.

* * * * *